(12) United States Patent
Tsutsui et al.

(10) Patent No.: US 6,750,967 B2
(45) Date of Patent: Jun. 15, 2004

(54) LIGHT SCATTERING MEASURING PROBE

(75) Inventors: Kazunori Tsutsui, Hirakata (JP); Tsutomu Mizuguchi, Shiga (JP)

(73) Assignee: Otsuka Electronics Co., Ltd., Hirakata (JP)

( * ) Notice: Subject to any disclaimer, the term of this patent is extended or adjusted under 35 U.S.C. 154(b) by 0 days.

(21) Appl. No.: 10/258,882

(22) PCT Filed: Feb. 28, 2002

(86) PCT No.: PCT/JP02/01831

§ 371 (c)(1),
(2), (4) Date: Oct. 30, 2002

(87) PCT Pub. No.: WO02/071035

PCT Pub. Date: Sep. 12, 2002

(65) Prior Publication Data

US 2003/0133112 A1 Jul. 17, 2003

(30) Foreign Application Priority Data

Mar. 1, 2001 (JP) .......................................... 2001-57203

(51) Int. Cl.⁷ .............................................. G01N 21/00
(52) U.S. Cl. ..................... 356/338; 250/227.21; 356/73
(58) Field of Search ............................... 356/336, 337, 356/338, 342, 343, 352; 250/574, 525, 341, 227.21, 227.11, 227.16, 227.28

(56) References Cited

U.S. PATENT DOCUMENTS

| | | | | | |
|---|---|---|---|---|---|
| 4,529,306 A | * | 7/1985 | Kilham et al. | ........... | 356/237.1 |
| 4,560,881 A | * | 12/1985 | Briggs | ..................... | 250/458.1 |
| 4,707,134 A | * | 11/1987 | McLachlan et al. | ........ | 356/342 |
| 4,753,530 A | * | 6/1988 | Knight et al. | .................. | 356/73 |
| 5,013,150 A | * | 5/1991 | Watts et al. | ................... | 356/73 |
| 5,046,854 A | * | 9/1991 | Weller et al. | ............... | 356/440 |
| 5,155,549 A | * | 10/1992 | Dhadwal | ..................... | 356/336 |
| 5,170,056 A | * | 12/1992 | Berard et al. | ............. | 250/341.2 |
| 5,202,558 A | * | 4/1993 | Barker | .................. | 250/227.21 |
| 5,815,264 A | * | 9/1998 | Reed et al. | .................. | 356/336 |
| 6,075,601 A | * | 6/2000 | Marcus et al. | .............. | 356/450 |

FOREIGN PATENT DOCUMENTS

| | | |
|---|---|---|
| JP | 4-29860 | 3/1992 |
| JP | 5-10884 | 1/1993 |
| JP | 5-149862 | 6/1993 |
| JP | 6-3550 | 1/1994 |
| JP | 9-80259 | 3/1997 |
| JP | 10-281976 | 10/1998 |
| JP | 11-352333 | 12/1999 |
| WO | WO 00/31514 | 6/2000 |

OTHER PUBLICATIONS

Khan et al.; "Design and Characterization of Coherent Integrated Fiber–Optic Imaging Probes", Applied Optics, vol. 33, No. 25, pp. 5875–5881, (1994).

* cited by examiner

Primary Examiner—Frank G. Font
Assistant Examiner—Sang H. Nguyen
(74) Attorney, Agent, or Firm—Finnegan, Henderson, Farabow, Garrett & Dunner, L.L.P.

(57) ABSTRACT

The constitution of a probe for measuring light scattering according to this invention is as follows: a light input optical fiber 4 and a scattered light measuring optical fiber 6 for collecting and transmitting scattered light are inserted into a main body of the probe 3; the optical fiber 4 is passed through a hole provided in the probe 3 for measuring light scattering to extend outward; an end portion of each of the optical fibers 4, 6 is covered with a ferrule 66 or 67; an end of each of the ferrules 66, 67 is cut into the shape of a truncated cone such that a part of or the entire end face of the optical fiber 4 or 6 remains; and the ferrules 66, 67 are held by a support body 70 and the like in such a manner that the end faces of the optical fibers 4, 6 are disposed to be adjacent to each other at a predetermined angle with a predetermined distance in between. Accordingly, the end portions of the optical fibers can be reinforced and protected by the ferrules even when they have poor strength. In addition, cutting the ends of the ferrules into the shape of a truncated cone allows the distance between the end faces of the optical fibers to be reduced.

8 Claims, 5 Drawing Sheets

(a)

(b)

LIGHT SCATTERING MEASURING PROBE

TECHNICAL FIELD

The present invention relates to a probe for measuring light scattering which performs light scattering measurements by illuminating a sample with light and detecting light scattered from inside a scattering volume.

BACKGROUND ART

An instrument for measuring light scattering refers to an instrument that measures fluctuation, or change with time, in intensity of scattering light caused by motion of particles present in a fluid (Brownian Motion), thereby determining the diffusion coefficient and hydrodynamic size of the particles.

In a conventional instrument for measuring light scattering, measurements are carried out by illuminating a cell shaped as a cylinder or a rectangular parallelepiped filled with a sample fluid with a laser beam through a lens, passing scattered light emitted from the sample through a light-receiving system in which the observation volume is limited by a pinhole or the like, and measuring the scattered light by means of a photodetector such as a photo multiplier.

In the above instrument for measuring light scattering, the light path length in the cell of the sample fluid is long. Accordingly, as the concentration of particles in the solution increases, scattering by the scattered light, or multiple scattering, occurs in the cell, making it impossible to obtain accurate information on the scattered light.

In order to overcome this inconvenience, there has been proposed a structure of a probe for measuring light scattering (R. R. Khan, H. S. Dhadwal, and K. Suh, Applied Optics 33(25), 1994), in which an end of a light input optical fiber and an end of a light receiving optical fiber are disposed in the cell at a predetermined angle in close proximity to each other. This probe for measuring light scattering allows the observation volume to be small, thereby precluding the problem of multiple scattering.

In the above mentioned probe for measuring light scattering, a micro lens or a graded-index fiber for bringing the focus of each optical fiber onto the intended position is disposed at the end face of each of the light input fiber and the light receiving fiber. Accordingly, high accuracy is required for positioning each optical fiber at each lens, making it difficult to keep the product quality at a practical level.

The basic structure of an optical fiber comprises a core that propagates light, and a cladding with a small refractive index surrounding the core, which is further covered with a resin coating for protection.

Relating to this, an invention has been disclosed as PCT International Publication No. WO00/31514, in which the cladding is exposed by removing the resin coating around the optical fiber, or the core is exposed by removing the cladding as well so that the distance between the end faces of the cores is made as small as possible so as not to be affected by multiple scattering.

However, in such a structure with the cladding or the core being exposed, the following problems arise: it is impossible to keep the strength of the optical fibers, adjustment of the positions of the cores is difficult, and light leaks from the cladding.

It is therefore an object of this invention to provide a probe for measuring light scattering that is easy to produce, and capable of measuring intensity of scattered light with high accuracy and high reliability.

SUMMARY OF THE INVENTION

A probe for measuring light scattering in accordance with the present invention comprises a light input optical fiber for transmitting light for illuminating a sample therewith, and a scattered light measuring optical fiber for collecting and transmitting scattered light. An end portion of each of the optical fibers is covered with a ferrule, an end of the ferrule being cut into the shape of a truncated cone such that a part of or the entire end face of the optical fiber remains. The ferrules are held by the probe for measuring light scattering in such a manner that the end faces of the optical fibers are disposed to be adjacent to each other at a predetermined angle with a predetermined distance in between.

Being arranged as above, the end portions of the optical fibers can be reinforced and protected by the ferrules even when they have poor strength. In addition, the distance and angle between the end faces of the optical fibers can be easily maintained by holding the ferrules. The ferrules also prevent light from leaking from the claddings.

Furthermore, as a result of cutting the ends of the ferrules into the shape of a truncated cone, bubbles in the sample fluid are less likely to adhere to the ends of the optical fibers. Also, the distance between the end faces of the optical fibers can be reduced in this arrangement as compared with cases where the ferrules are not tapered.

The angle and distance between the end faces of the optical fibers are preferably adjustable through the ferrules by an adjustment member. By this arrangement, it is possible to control the scattering volume to be a desired volume.

This adjustment can be performed precisely and easily by the use of screws.

The optical fibers are preferably single-mode optical fibers. This allows measurements to be performed in a condition where the coherence is improved.

The ferrules preferably have cladding portions of the optical fibers inserted therein excluding coating portions of the optical fibers. This makes it possible to taper the ends of the ferrules such that the cladding portions or the cladding portions and core portions inside thereof are cut obliquely. Accordingly, reducing the distance between the end faces of the optical fibers can be easily accomplished.

BEST MODE FOR CARRYING OUT THE INVENTION

Figure 1:
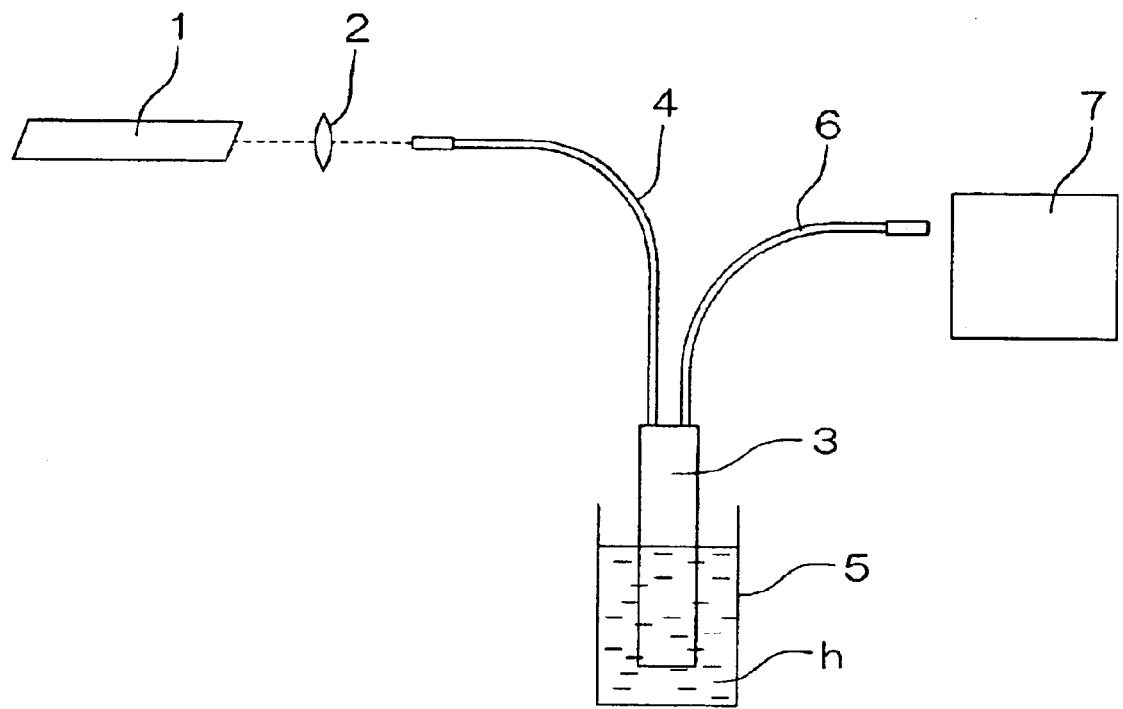
FIG. 1 shows the overall configuration of a measuring system including a probe 3 for measuring light scattering.

FIG. 1 shows the overall configuration of a measuring system including a probe 3 for measuring light scattering. Light launched from laser equipment 1 is focused by a lens 2 to enter a light input optical fiber 4. An end of the light input optical fiber 4 is connected to a probe 3 for measuring light scattering. The probe 3 for measuring light scattering is inserted into a cell 5 that is filled with a sample fluid h so that the sample fluid h is illuminated with a laser beam emitted from the probe 3 for measuring light scattering.

Light scattered from the sample h is received by the probe 3 for measuring light scattering and passes through the probe 3 for measuring light scattering and a scattered light measuring optical fiber 6, and then enters a photodetector 7 such as a photomultiplier, where data in time sequence are measured. Thereafter, at a processing circuit not shown in the drawing, the autocorrelation coefficient of the data is calculated, thereby obtaining the particle size and the like.

The light input optical fiber 4 and scattered light measuring optical fiber 6 are preferably single-mode optical fibers in view of maintaining the coherence of light.

Figure 2:
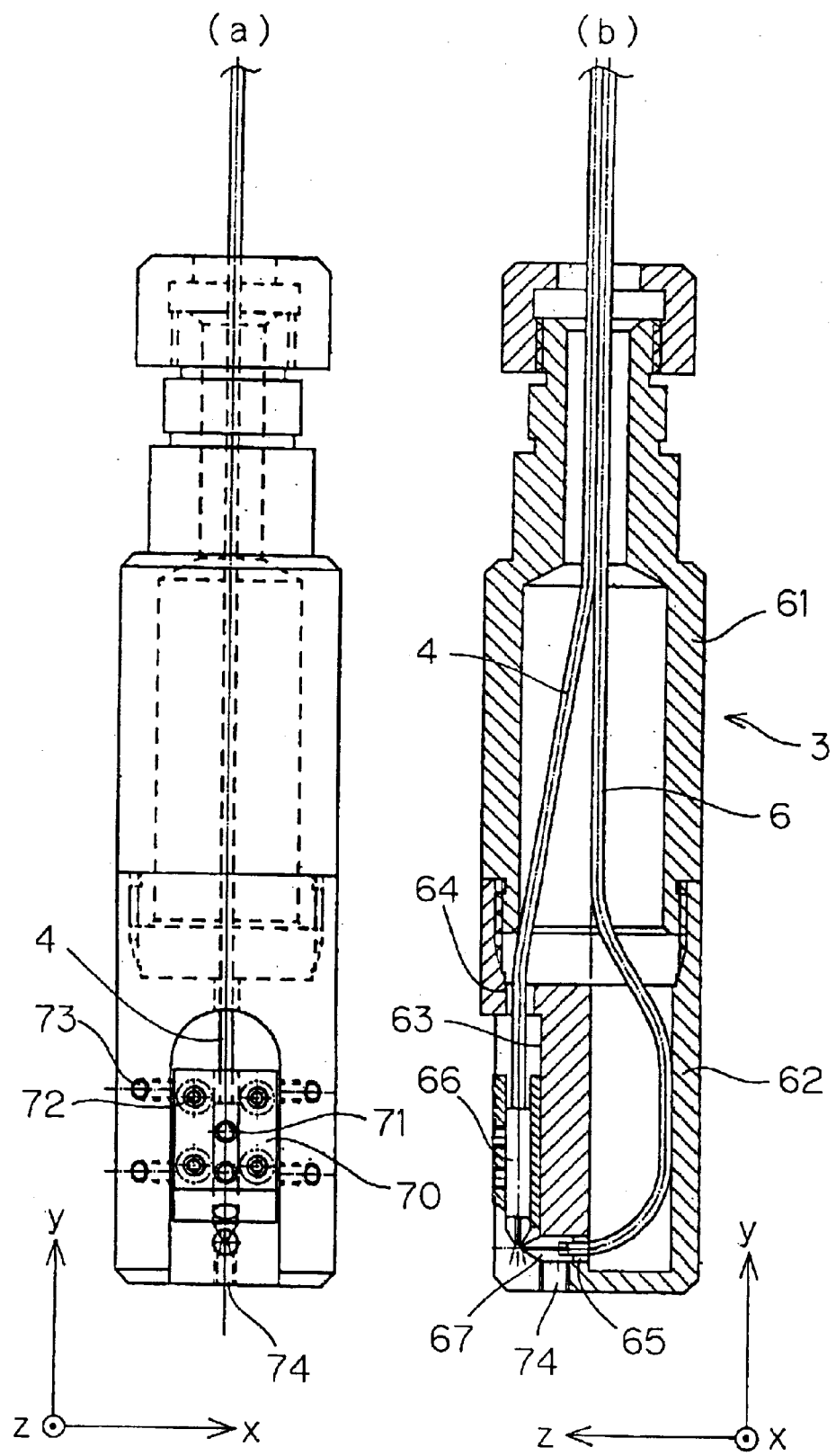
FIG. 2 shows an elevational view (a) and a sectional side elevation view (b) of the probe 3 for measuring light scattering.

FIG. 2 shows an elevational view (a) and a sectional side elevation view (b) taken along the center line of the probe 3 for measuring light scattering. The vertically upward direction, the front side direction, and the right side direction are indicated by y, z, and x, respectively.

The probe 3 for measuring light scattering has a cylindrical trunk portion 61 and an end portion 62 that is coupled with the trunk portion 61. The light input optical fiber 4 and scattered light measuring optical fiber 6 are inserted such that they penetrate through the trunk portion 61 and the end portion 62. The trunk portion 61 and the end portion 62 may be made of metal or resin.

A recess 63 is formed in a plane of the end portion 62. The light input optical fiber 4 sticks out of a vertical hole 64 formed in the recess 63, and the scattered light measuring optical fiber 6 is extended to a horizontal hole 65 formed in the recess 63.

The end portion of the light input optical fiber 4 that sticks out is covered with a cylindrical ferrule 66, and the end portion of the scattered light measuring optical fiber 6 is covered with a ferrule 67. FIG. 2 shows the ferrule 66 partly in cross section, and the ferrule 67 entirely in cross section.

The ferrule 66 penetrates a hole provided in the box-shaped support body 70. The ferrules 66, 67 are disposed adjacent to each other at an angle of 90 degrees. (See also FIG. 5.) The scattering volume to be measured is indicated by the symbol V in FIG. 5.

In the front surface and the side surfaces of the support body 70, and the bottom surface of the end portion 62, as will be later described in detail, adjusting screws 71–74 are provided as the "adjustment member" for adjusting the position of the optical fiber 4 for emitting light, and the position of the optical fiber 6 for receiving light.

Figure 3:
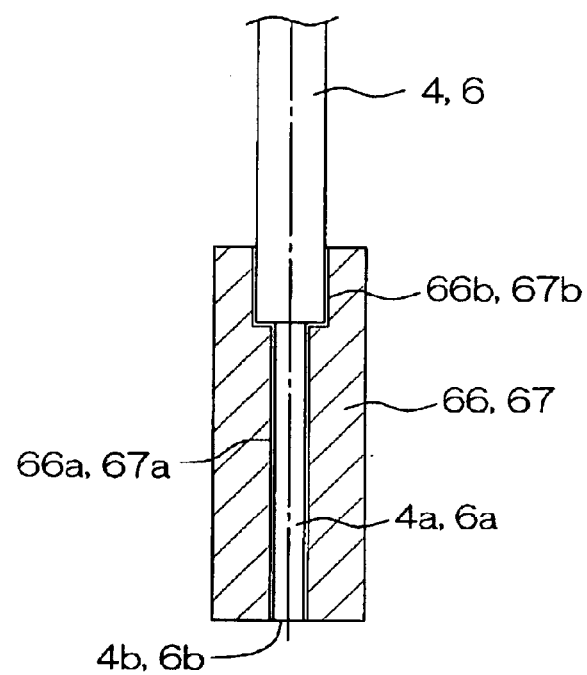
FIG. 3 shows cross-sectional views of ferrules 66, 67, illustrating details thereof. The ferrule(s) before cutting is shown in (a), and the ferrule (s) after cutting is shown in (b).
Figure 3:
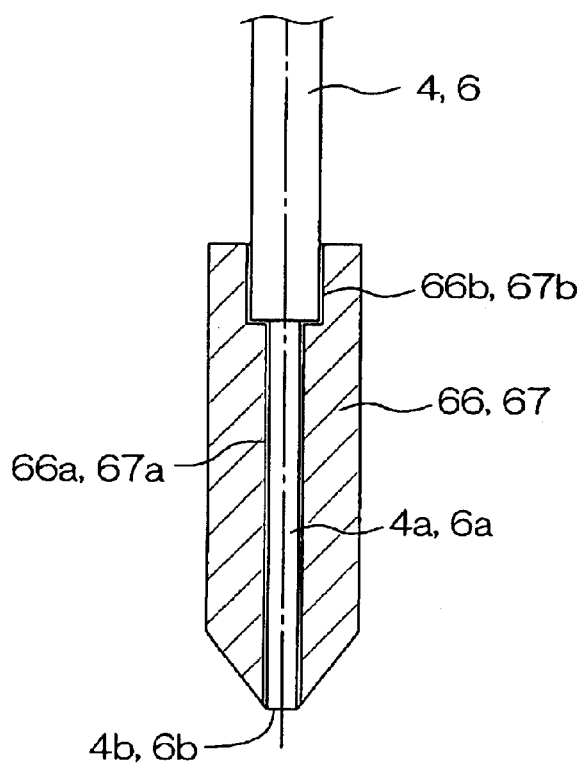

FIG. 3 shows cross-sectional views of the ferrules 66, 67, illustrating details thereof. The ferrules 66, 67 are made of ceramics such as zirconia and cylindrically shaped.

The light input optical fiber 4 and the scattered light measuring optical fiber 6 have cladding portions 4a and 6a, respectively, which are exposed. Narrow holes 66a, 67a into which the exposed portions are inserted are provided along the center lines of the ferrules 66, 67, respectively. In addition, wide holes 66b, 67b into which coated portions of the light input optical fiber 4 and scattered light measuring optical fiber 6 are fitted are provided at the upper ends of the ferrules 66, 67, respectively.

The lower ends of the ferrules 66, 67 are polished into the shape of a truncated cone in such a manner that a part of or the entire end faces of the optical fibers 4, 6 remain. (See FIG. 3(b).) The polishing may or may not reach the cladding portions 4a, 6a. Or, the polishing may proceed beyond the cladding portions 4a, 6a, reaching core portions inside thereof.

The remaining end faces 4b, 6b must include the core portions where light is propagated through the optical fibers 4, 6.

By such angled polishing, the end faces 4b, 6b of the optical fibers 4, 6 can be disposed in sufficiently close proximity to each other. Moreover, since bubbles in the sample become less likely to adhere to the end faces 4b, 6b, the reliability of measurements can be enhanced.

Figure 4:
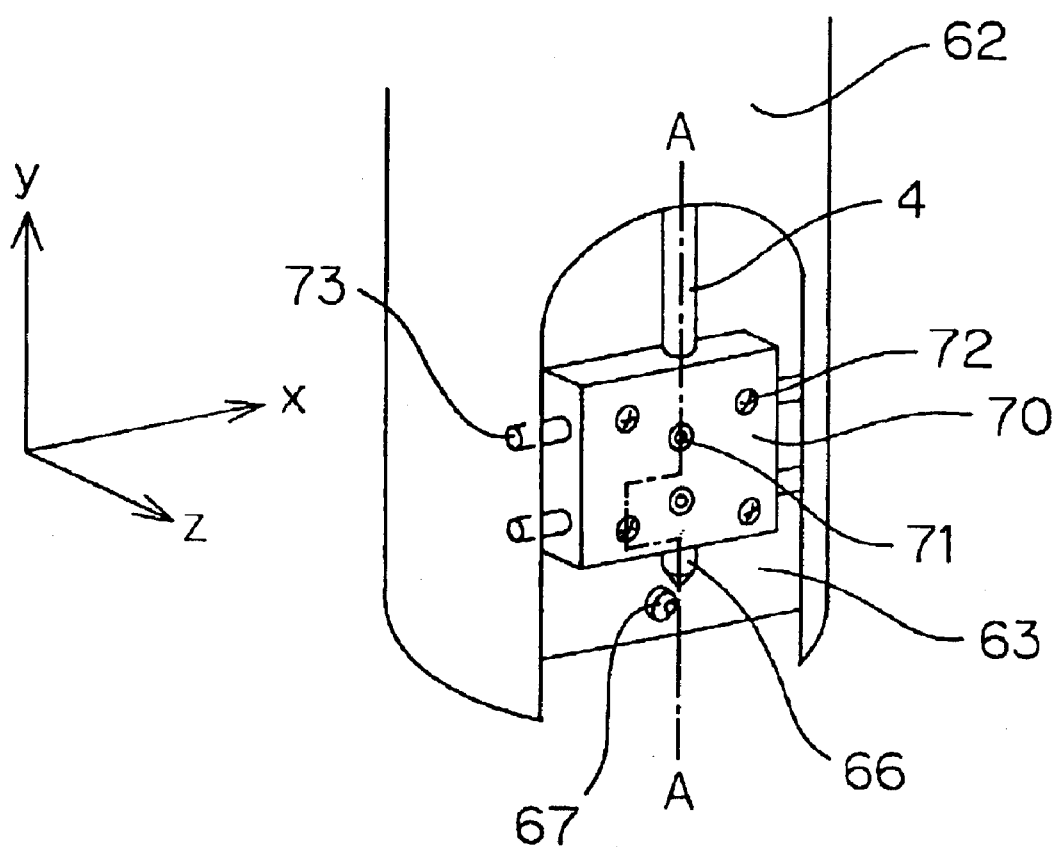
FIG. 4 is a perspective view showing a support body 70 and so on disposed in a recess 63 of an end portion 62.
Figure 5:
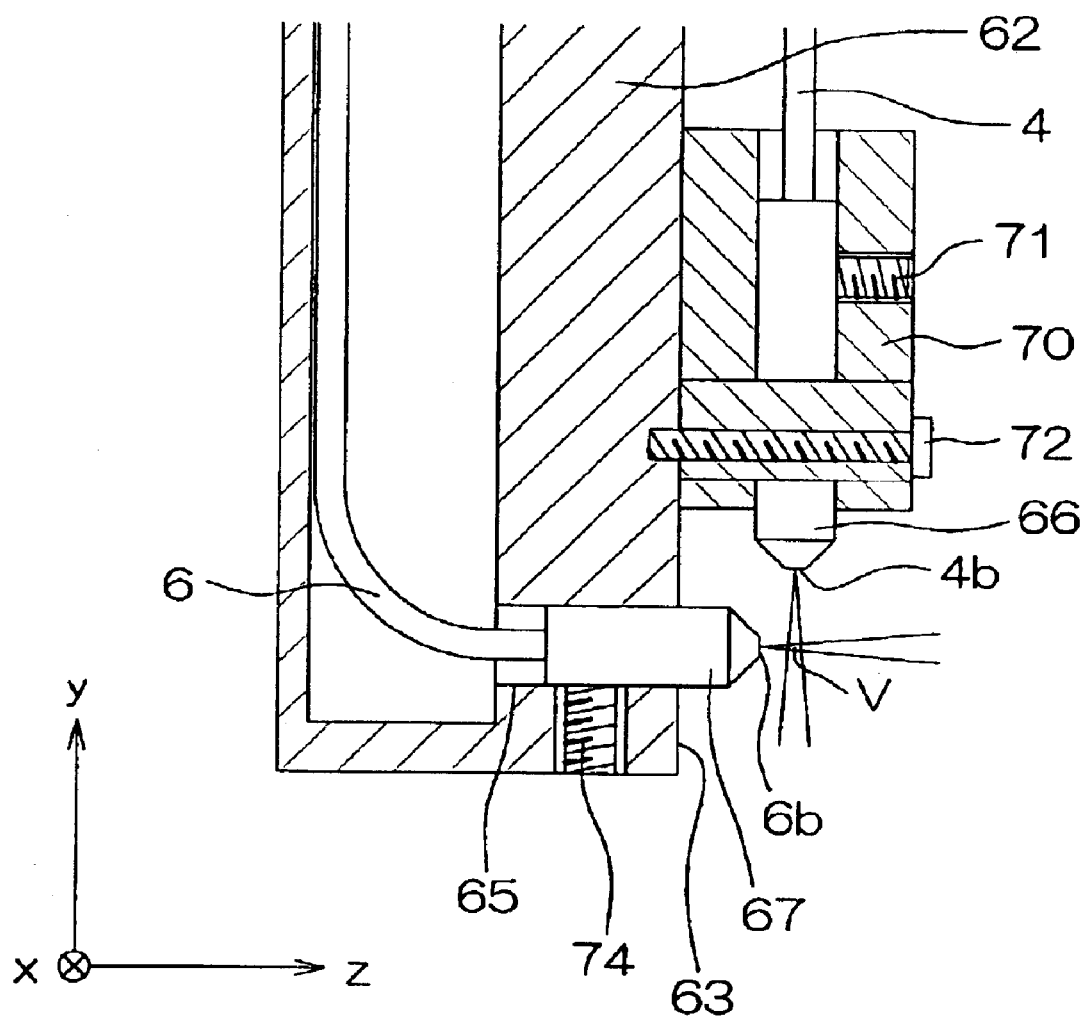
FIG. 5 is a cross-sectional view taken along the stepped line A—A in FIG. 4.

The mechanism for adjusting the positions of the end faces 4b, 6b of the optical fibers 4, 6 is now described referring to FIGS. 4, 5.

FIG. 4 is a perspective view showing the support body 70 and so on disposed in the recess 63 of the end portion 62, and FIG. 5 is a cross-sectional view taken along the stepped line A—A in FIG. 4.

Fixing screws 72 for fixing the support body 70 to the recess 63 in the end portion 62 are inserted into the support body 70. Also, adjusting screws 71 are provided, which are fastened after being loosened so as to carry out adjustment by moving the ferrule 66 and the light input optical fiber 4 in the direction of y axis.

Adjusting screws 73 are provided for carrying out adjustment by moving the support body 70 in the direction of x axis. Meanwhile, when adjustment is carried out by means of the adjusting screws 73 by moving the support body 70 in the direction of x axis, the fixing screws 72 are first loosened, which is followed by adjustment by the adjusting screws 73, and thereafter the fixing screws 72 are fastened. For this reason, the screw holes of the fixing screws 72 have some allowance.

In addition, an adjusting screw 74 is provided in the bottom surface of the end portion 62 as shown in FIG. 5. It is fastened after being loosened for adjusting the position of the ferrule 67 and the scattered light measuring optical fiber 6 in the direction of z axis.

By turning the above mentioned screws 71, 73, 74, the angle and distance between the end face 4b of the light input optical fiber 4 and the end face 6b of the scattered light measuring optical fiber 6 can be finely adjusted.

With the probe 3 for measuring light scattering arranged in the above manner being dipped in the sample fluid h, when a laser beam enters the light input optical fiber 4, scattered light is emitted through the scattered light measuring optical fiber 6. This scattered light can be detected by the photodetector 7. It is possible to measure a very small scattering volume V by bringing the ferrules 66, 67 having tapered ends in proximity to each other. It is therefore possible to prevent the accuracy of measurements from lowering due to multiple scattering.

While a preferred embodiment of the present invention has been described, it is to be understood that the present invention is not limited to this specific mode, but various modifications are possible without departing from the spirit and scope of the invention.

What is claimed is:

1. A probe for measuring light scattering which performs light scattering measurements by illuminating a sample with light and detecting light scattered from inside a scattering volume in the sample, the probe comprising:

a light input optical fiber for transmitting light to a sample for illuminating a scattering volume in the sample therewith; and a scattered light measuring optical fiber for collecting scattered light from the scattering volume and transmitting the scattered light, wherein both said optical fibers are inserted into the and an end portion of each of the optical fibers is covered with a ferrule, an end of each ferrule being cut into the shape of a truncated cone such that a part of or the entire end face of the optical fiber including a core thereof remains exposed at said end of the ferrule and wherein the ferrules are held by the probe so that the end faces of the optical fibers are disposed adjacent to each other at a predetermined angle with a predetermined distance in between.

2. The probe for measuring light scattering according to claim 1, wherein the angle and distance between the end faces of the optical fibers are adjustable through the ferrules by means of an adjustment member.

3. The probe for measuring light scattering according to claim 2, wherein the adjustment member includes a support body provided in a main body of the probe, the support body having a first hole for inserting one of the ferrules thereinto in one direction, and a first screw provided in the support body for fixing the ferrule that is inserted in the first hole.

4. The probe for measuring light scattering according to claim 3, wherein the support body is movable in a direction perpendicular to the direction in which the ferrule is inserted, and fixable in place by a second screw to the main body of the probe after it is moved.

5. The probe for measuring light scattering according to claim 4, further comprising a third screw for moving the support body in the direction perpendicular to the direction in which the ferrule is inserted.

6. The probe for measuring light scattering according to claim 3, wherein the adjustment member includes a second hole provided in the main body of the probe for inserting the other of the ferrules thereinto in another direction, and a fourth screw provided in the main body of the probe for fixing the other ferrule that is inserted in the second hole.

7. The probe for measuring light scattering according to claim 1, wherein the optical fibers are single-mode optical fibers.

8. The probe for measuring light scattering according to claim 1, wherein each of the ferrules includes a cladding portion of each of the optical fibers inserted therein.

* * * * *

UNITED STATES PATENT AND TRADEMARK OFFICE
CERTIFICATE OF CORRECTION

PATENT NO. : 6,750,967 B2
DATED : June 15, 2004
INVENTOR(S) : Kazunori Tsutsui et al.

It is certified that error appears in the above-identified patent and that said Letters Patent is hereby corrected as shown below:

Column 5,
Line 4, after "inserted into the", insert -- probe --.

Signed and Sealed this

Sixteenth Day of November, 2004

JON W. DUDAS
*Director of the United States Patent and Trademark Office*